(12) United States Patent
Elliott et al.

(10) Patent No.: US 11,129,575 B2
(45) Date of Patent: *Sep. 28, 2021

(54) PERSONAL HEALTH DATA COLLECTION

(71) Applicant: Leman Micro Devices SA, Lausanne (CH)

(72) Inventors: Christopher Elliott, Surrey (GB); Mark-Eric Jones, Cossonay-Ville (CH); Mark Bennett, Surrey (GB); Mikhail Nagoga, Pully (CH)

(73) Assignee: Leman Micro Devices SA, Lausanne (CH)

( * ) Notice: Subject to any disclaimer, the term of this patent is extended or adjusted under 35 U.S.C. 154(b) by 164 days.

This patent is subject to a terminal disclaimer.

(21) Appl. No.: 16/424,994

(22) Filed: May 29, 2019

(65) Prior Publication Data

US 2019/0320984 A1    Oct. 24, 2019

Related U.S. Application Data

(63) Continuation of application No. 14/127,727, filed as application No. PCT/GB2012/000549 on Jun. 26, 2012, now Pat. No. 10,342,493.

(30) Foreign Application Priority Data

Jun. 30, 2011 (GB) ........................................ 1111138
Jan. 18, 2012 (GB) ..................................... 1200794

(51) Int. Cl.
*A61B 5/00* (2006.01)
*A61B 5/022* (2006.01)
(Continued)

(52) U.S. Cl.
CPC ........ *A61B 5/6898* (2013.01); *A61B 5/02055* (2013.01); *A61B 5/0261* (2013.01);
(Continued)

(58) Field of Classification Search
CPC .. G01K 13/002; G01K 13/20; A61B 5/14532; A61B 5/02125; A61B 5/1455;
(Continued)

(56) References Cited

U.S. PATENT DOCUMENTS 4,718,426 A    1/1988 Russell
4,882,492 A    11/1989 Schlager
(Continued)

FOREIGN PATENT DOCUMENTS

DE    10 2004-001931 A1    8/2005
DE    10 2005-004143 A1    8/2006
(Continued)

OTHER PUBLICATIONS

Leslie, et al., Mobile Communications for Medical Care, Final Report, Apr. 21, 2011, pp. 1-120.
(Continued)

*Primary Examiner* — Michael J Tsai
*Assistant Examiner* — Patrick M Mehl
(74) *Attorney, Agent, or Firm* — BakerHostetler

(57) ABSTRACT

The present invention provides a personal hand-held monitor comprising a signal acquisition device for acquiring signals which can be used to derive a measurement of a parameter related to the health of the user, the signal acquisition device being integrated with a personal hand-held computing device. The present invention also provides a signal acquisition device adapted to be integrated with a personal hand-held computing device to produce a personal hand-held monitor as defined above.

17 Claims, 9 Drawing Sheets

(51) Int. Cl.
*A61B 5/026* (2006.01)
*A61B 5/0205* (2006.01)
*A61B 5/1455* (2006.01)
*A61B 5/021* (2006.01)
*A61B 5/145* (2006.01)
*G01K 13/20* (2021.01)
*A61B 5/332* (2021.01)
*A61B 7/02* (2006.01)
*A61B 8/06* (2006.01)
*A61B 5/01* (2006.01)

(52) U.S. Cl.
CPC ...... *A61B 5/02125* (2013.01); *A61B 5/02225* (2013.01); *A61B 5/02233* (2013.01); *A61B 5/02241* (2013.01); *A61B 5/1455* (2013.01); *A61B 5/14532* (2013.01); *A61B 5/14551* (2013.01); *A61B 5/332* (2021.01); *A61B 5/742* (2013.01); *A61B 5/7405* (2013.01); *G01K 13/20* (2021.01); *A61B 5/01* (2013.01); *A61B 7/02* (2013.01); *A61B 8/06* (2013.01); *A61B 2560/0252* (2013.01); *H04M 2250/12* (2013.01)

(58) Field of Classification Search
CPC ............ A61B 5/02055; A61B 5/14551; A61B 5/02241; A61B 5/0404; A61B 2560/0252; A61B 5/01; A61B 8/06; A61B 7/02; A61B 5/6898; A61B 5/332; A61B 5/02233; A61B 5/0261; A61B 5/7405; A61B 5/742; A61B 5/02225; A61B 7/045; A61B 8/4427; A61B 8/488; A61B 7/00; A61B 5/08; H04M 2250/12
See application file for complete search history.

(56) References Cited

U.S. PATENT DOCUMENTS

| | | | |
|---|---|---|---|
| 5,050,612 A | 9/1991 | Matsumura | |
| 5,140,990 A | 8/1992 | Jones et al. | |
| 5,862,805 A | 1/1999 | Nitzan | |
| 5,865,755 A | 2/1999 | Golub | |
| 6,159,157 A | 12/2000 | Archibald et al. | |
| 6,302,844 B1 | 10/2001 | Walker | |
| 6,340,349 B1 | 1/2002 | Archibald et al. | |
| 6,511,436 B1 | 1/2003 | Asmar | |
| 7,396,331 B2 | 7/2008 | Mack et al. | |
| 7,641,614 B2 * | 1/2010 | Asada ............... | A61B 5/6838 600/485 |
| 2003/0036685 A1 | 2/2003 | Goodman | |
| 2005/0234310 A1 | 10/2005 | Alwan et al. | |
| 2007/0093701 A1 | 4/2007 | Myers et al. | |
| 2007/0100213 A1 | 5/2007 | Dossas et al. | |
| 2007/0100243 A1 | 5/2007 | Lam et al. | |
| 2007/0285226 A1 | 12/2007 | Yi | |
| 2009/0216132 A1 * | 8/2009 | Orbach ............... | A61B 5/7445 600/485 |
| 2010/0106029 A1 | 4/2010 | Fraden | |
| 2010/0204588 A1 * | 8/2010 | Kim ..................... | A61B 5/021 600/485 |
| 2011/0237905 A1 | 9/2011 | Kutzik et al. | |
| 2012/0128143 A1 | 5/2012 | Rudman | |

FOREIGN PATENT DOCUMENTS

| | | |
|---|---|---|
| EP | 0041696 A1 | 12/1981 |
| EP | 2191771 A1 | 6/2010 |
| JP | 2001/190507 A1 | 7/2001 |
| JP | 2003-290226 | 10/2003 |
| JP | 2005-148038 A | 6/2005 |
| JP | 2006-072665 A | 3/2006 |
| JP | 2006/239114 A | 9/2006 |
| JP | 2010513911 A | 4/2010 |
| JP | 2010-531154 | 9/2010 |
| JP | 2010-220949 A | 10/2010 |
| WO | 09203967 A2 | 3/1992 |
| WO | 2001-65810 A1 | 9/2001 |
| WO | 2002030277 A2 | 4/2002 |
| WO | 2008078271 A1 | 7/2008 |
| WO | 2008-110949 | 9/2008 |
| WO | 2010-017973 A | 2/2010 |
| WO | 2011-073894 A | 6/2011 |

OTHER PUBLICATIONS

Ladeira, et al., Strategic Applications Agenda, Version 3, Working Group on Leading Edge Applications, Jan. 2010, www.emobility.eu.org; 396 pages.

Azmal, et al., Intl. Conf. Biomedical and Pharmaceutical Engineering 2006 (ICBPE 2006), pp. 504-507.

Healthcare unwired, Health Research Institute, New business models delivering care anywhere, PricewaterhouseCoopers, Sep. 2010, 40 pages.

Gee, Tim, Apple Targets Health Care with iPhone 3.0 OS, Medical Connectivity, http://medicalconnectivity.com/2009/03/19/apple-targets-health-care-with-iphone-30-os/, pp. 1-13.

Padilla, et al., Cardiovasc Eng., Pulse Wave Velocity and digital volume pulse as indirect estimators of blood pressure: Pilot study on Healthy Volunteers, 2009, 9 pages.

Teng, et al., Proceedings of the 25th Annual International Conference of the IEEE EMBS, Cancun, Mexico, Sep. 17-21, 2003, 4 pages, 3153-3156.

Chua, et al. Freescale Semiconductor Application Note AN1571, Digital Blood Pressure Meter, 2005, pp. 1-8.

Reisner, et al., Anesthesology 2008, Utility of the Photoplethysmogram in Circulatory Monitoring, vol. 108, No. 5, pp. 950-958.

Al-Jaafreh, et al,, EMBS Annual International Conference, Proceedings of the 28th IEEE, New Model to estimate Mean Blood Pressure by Heart Rate with Stroke Volume changing influence, Aug. 30-Sep. 3, 2006, pp. 1803-1805.

Allen, Physiological Measurement, Photoplethysmography and its application i clinical physiological measurement, 2007, 28: pp. R1-R39.

* cited by examiner

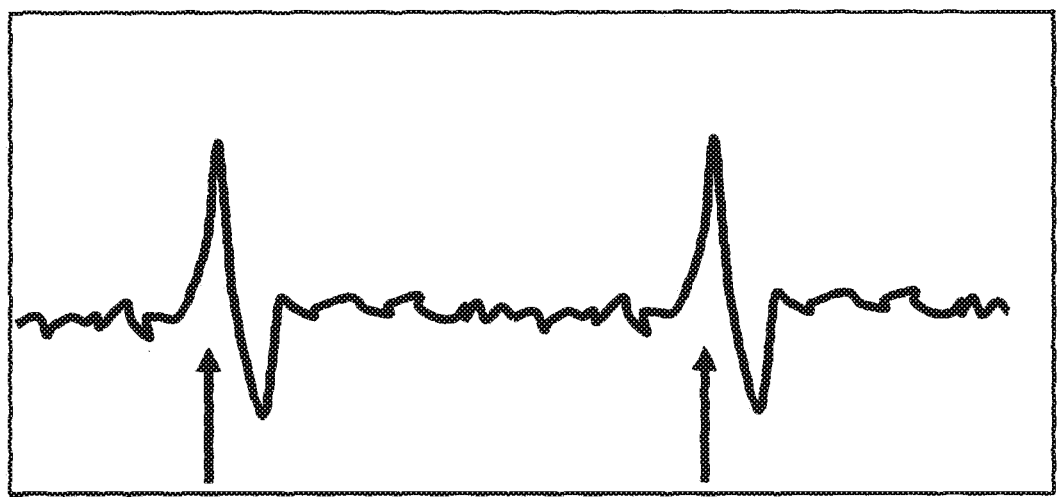
Figure 1: The amplified and filtered potential difference.
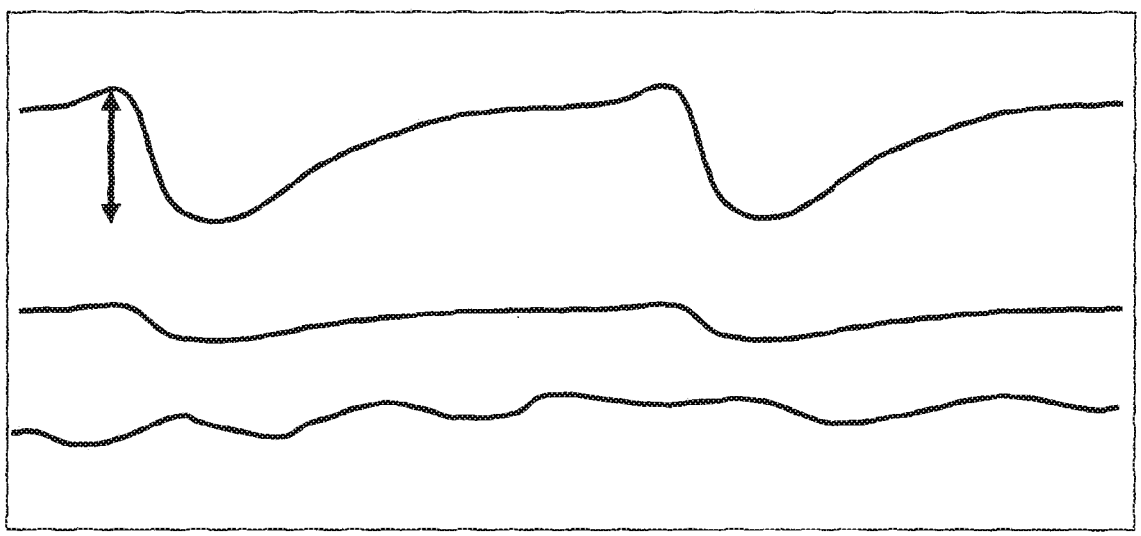
Figure 2: Schematic drawings of PPG signals

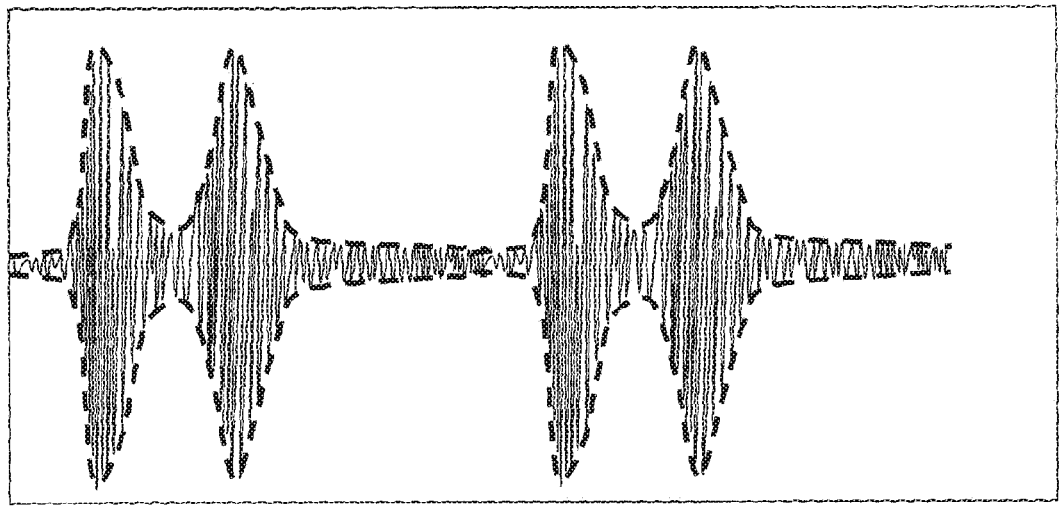
Figure 3: signal collected by the acoustic sensor
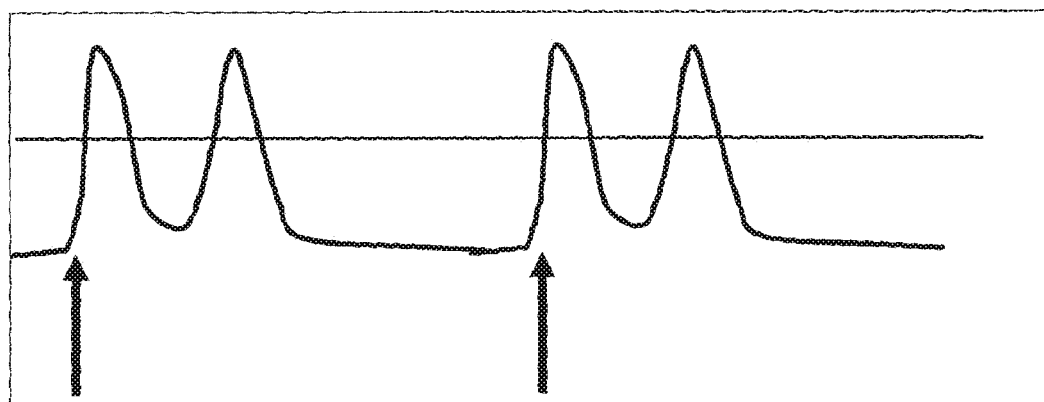
Figure 4: The acoustic envelope.

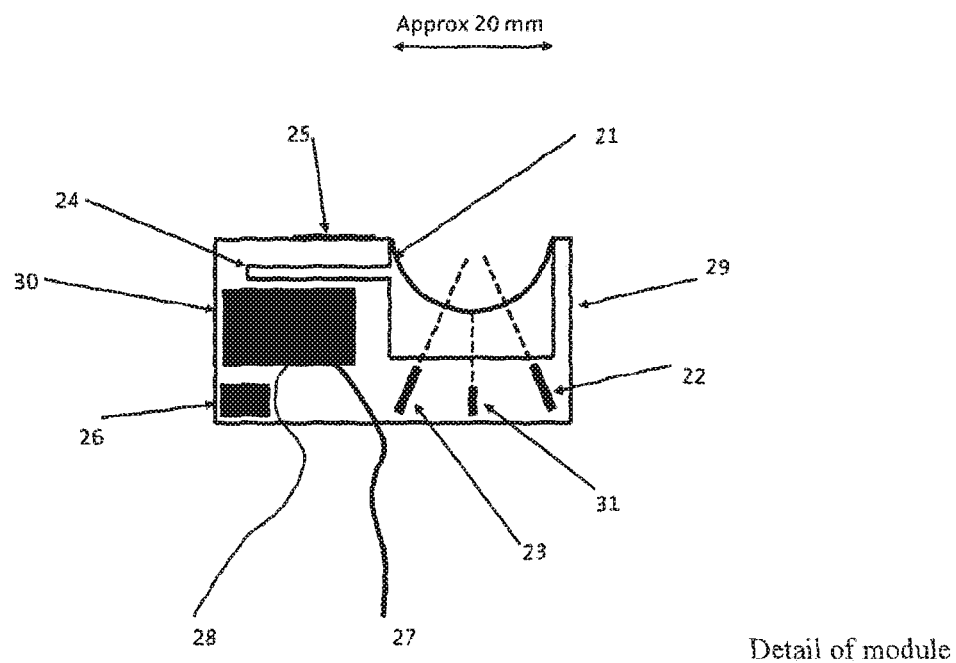
Detail of module
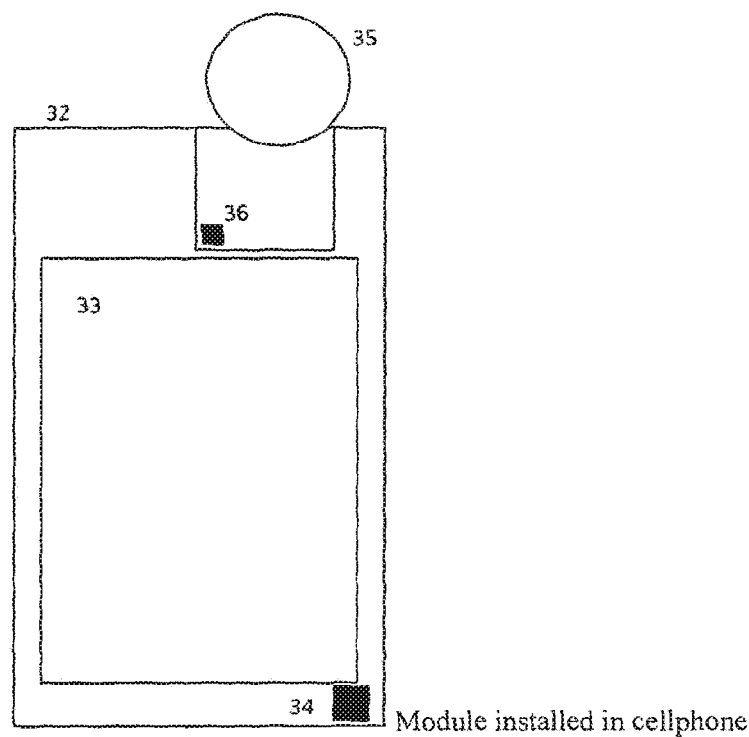
Module installed in cellphone
Figure 6

Approx 20 mm
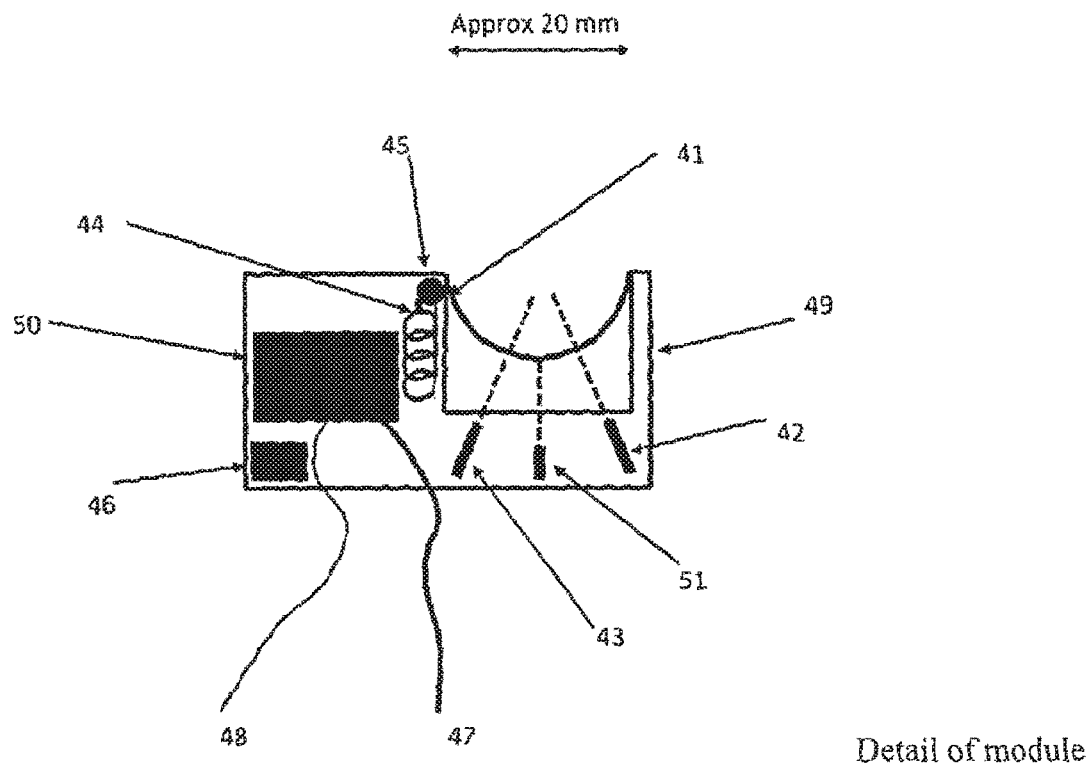
Detail of module
Not to scale
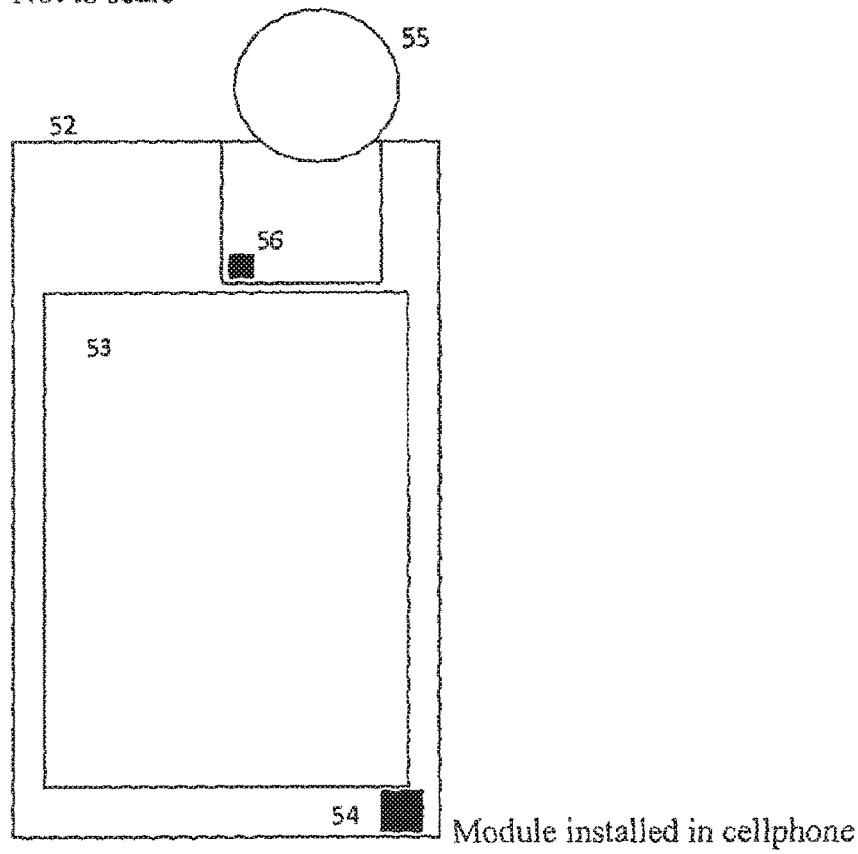
Module installed in cellphone
Figure 7

PERSONAL HEALTH DATA COLLECTION

CROSS-REFERENCE TO RELATED APPLICATIONS

This application is a continuation application of U.S. patent application Ser. No. 14/127,727, filed on Sep. 18, 2014, which is a national stage application of international patent application no. PCT/GB2012/000549, filed Jun. 26, 2012, which claims the benefit of United Kingdom patent application no. 1111138.2, filed Jun. 30, 2011, and United Kingdom patent application no. 1200794.4, filed Jan. 18, 2012, the disclosures of all of which are hereby incorporated by reference as if set forth in their entireties herein.

FIELD OF THE INVENTION

The present invention relates to means for collecting personal health data. In particular, the invention relates a personal hand-held monitor (hereafter "a PHHM") comprising a signal acquisition device for acquiring signals which can be used to derive one or more measurements of parameters related to the health of a user, the signal acquisition device being integrated with a personal hand-held computing device (hereafter "a PHHCD"). The PHHM uses the processor of the PHHCD to control and analyse signals received from the signal acquisition device. The present invention also relates to a signal acquisition device adapted to be integrated with such a PHHCD. The present invention further relates to systems for operating the PHHM and for handling the signals acquired by the signal acquisition device. The present invention further relates to a system for analysing, storing and transmitting signals acquired by the PHHM via the Internet or for regulating the uses to which the data derived from those signals may be put.

BACKGROUND TO THE INVENTION

Cellphones (also known as mobile phones) are a part of everyday life. In the developed world, a large majority of adults have a cellphone. The use of cellphones is also becoming much more prevalent in developing countries as it enables such countries to develop a communications system without the need to install cabling. There have been various proposals for using cellphones in healthcare. However, all of these proposals have drawbacks.

Leslie, I et al., "Mobile Communications for medical care", Final Report, 21 Apr. 2011, reports on a major study by the University of Cambridge which identified the crucial contribution that cellphone networks will make to healthcare in developed, low income and emerging countries by transferring "vital signs" and other data from local measurement devices to a central data collection and processing computer. It identified two separate industrial communities—those who make cellphones and those who make medical devices.

Ladeira D et al., "Strategic Applications Agenda Version 3", Working Group on Leading Edge Applications, January 2010, www.emobility.eu.org, is an e-mobility study which considered the wide implications of networked health care and stated: "Smart phones can collect measurement results automatically and wirelessly from the measuring devices and seamlessly transfer the collected data to the doctor for further analysis."

"Healthcare unwired—new business models delivering care anywhere" PricewaterhouseCoopers' Health Research Institute, September 2010, is a study which addresses the opportunity presented by wide access to communications but from the perspective of the medical profession and its impact on the medical business model.

In a review in 2009, the Apple Company identified a growing demand for using its iPhone® as part of a communications chain from medical devices to practitioners and others (see http://medicalconnectivity.com/2009/03/19/apple-targets-health-care-with-iphone-30-os/.).

These reports are based on the use of existing medical devices and existing cellphone technology and therefore require the presence of both a medical device industry and a cellphone industry. It is an object of the present invention to enable collection of health-related data without the need for both these industries.

Tablet computers and portable personal computers are also becoming small enough to be used as PHHCDs. Many such devices also include communications facilities such as WiFi or wireless telephone connectivity.

Personal digital assistant devices ("PDAs") are also now well-known and include a processor for enabling a user to store and retrieve personal data.

THE PRESENT INVENTION

According to a first aspect of the present invention, there is provided a personal hand-held monitor (hereafter "a PHHM") comprising a signal acquisition device for acquiring signals which can be used to derive a measurement of a parameter related to the health of the user, the signal acquisition device being integrated with a personal hand-held computing device (hereafter "a PHHCD").

The PHHM of the present invention must be of such a size and weight that it can readily be manipulated by a normal adult using one hand to hold the PHHM and the other hand to enter or retrieve data. Preferably, the PHHCD includes communications facilities, such as WiFi or wireless telephone connectivity.

By "integrated" is meant that the signal acquisition device and the PHHCD form a single physical unit wherein the signal acquisition device and the PHHCD remain in fixed relationship when either is moved. All electrical connections are provided within the PHHM.

The acquired signals may be analogue or digital and, if analogue, may be converted to digital form for subsequent analysis by the processor of the PHHCD or for analysis by a remote data processing facility with which the PHHCD communicates using the Internet or other data communication means.

The PHHCD with which the signal acquisition device is integrated may be a cellphone, a tablet computer, a PDA or any other computing device which can readily be manipulated by a normal adult using one hand to hold the device and the other hand to enter or retrieve data.

The present invention merges medical technology with PHHCD technology by combining proven technological principles with novel implementation to create a PHHM which allows its user to acquire measurements of personal health data solely by using the PHHM. If desired, the user may communicate those measurements to other parties.

The use of the PHHM of the invention is a significant improvement over the use of the systems described in the studies referred to above because the signal acquisition device is integrated with the PHHCD. Since the signal acquisition device must be small enough to be integrated with the PHHCD without reducing its portability and is able to make use of the infrastructure of the PHHCD, such as its display and battery, it will be significantly less expensive than many of the known medical devices, which are too expensive for most users in low income or emerging countries and would deter even those in developed countries. The signal acquisition device exploits micro-electronic technology to reduce size and cost to a level at which the signal acquisition device integrated with a PHHCD can become ubiquitous and personal to the user.

Preferably, the signal acquisition device is adapted to acquire signals while in contact with or very close to one or more parts of the user's body. In particular, the signal acquisition device may be adapted to acquire signals while at least a part of it is in contact with:
- one or more of the user's digits, especially one or more fingers;
- the skin near the carotid artery;
- the user's chest, advantageously close to the heart; and/or
- the inside of a user's ear or mouth.

The signal acquisition device includes one or more sensors for acquiring signals which can be used to derive a measurement of a parameter which is useful in relation to personal health. Preferably, the one or more sensors is(are) for acquiring signals related to blood pressure, pulse wave velocity, blood pressure waveform, temperature, blood oxygen partial pressure, electrocardiogram, heart rate and/or respiratory rate. The signal acquisition device may include sensors for acquiring signals from which measurements of more than one of the above-mentioned parameters can be derived. The signal acquisition device preferably includes one or more sensor(s) for acquiring signals from which measurements of blood pressure, using, for instance, one or more of sphygmomanometry, photoplesthysmography and measurement of pulse wave velocity, can be derived.

The PHHM of the present invention may include one or more of the following sensors and means. Particularly preferred combinations of these sensors and means are referred to below.

Temperature Sensor

The signal acquisition device may include a temperature sensor for acquiring signals from which a measurement of local body temperature (i.e. the temperature near the location the sensor is applied to the body) can be derived by the processor of the PHHCD. Advantageously, the signal acquisition device also includes a sensor for acquiring signals from which a measurement of ambient temperature can be derived by the processor. This may be the same sensor as is used in connection with measuring local temperature or may be a separate sensor. Preferably, the processor is adapted to derive the user's core body temperature from the signals acquired by the temperature sensor.

As is well known, the temperature of a surface may be estimated by measuring the thermal radiation that it emits. For typical body temperatures, the radiation is concentrated at far infra-red wavelengths. It may be detected by a bolometer, in which a target is heated by the incident radiation and its temperature measured, either directly by detecting the change in its resistance or indirectly using a thermocouple, thermistor or other similar device. The field of view may be defined by a lens or window. The temperature sensor may be adapted to receive radiation from the inside of the ear or the temporal artery on the forehead as in existing medical devices using this technique.

The temperature sensor is preferably positioned so as to be able to sense the temperature of the user's ear, whether or not the user is making a telephone call.

Alternatively, the temperature sensor may be positioned so that it is able to make measurements of the surface temperature of the body part on which any other measurement made by the PHHM, such as a measurement of blood pressure, is to be made.

Alternatively, the temperature sensor may be located such that the user may orientate its direction by manipulating the PHHM such that it is able to sense the temperature of the body part or other item chosen, for example an item of the user's clothing. The processor of the PHHM may in this case be adapted to derive a signal indicative of ambient temperature and/or to provide instructions to the user to orient the PHHM so that signals indicative of body temperature and ambient temperature are obtained.

Alternatively, the temperature sensor may be located on an arm which can be brought into contact with one of the user's fingers or inserted into the user's ear or mouth. The arm may be fixed in position on the signal acquisition device or may be movable between an extended and a retracted position so that the arm can be retracted when not in use. The arm may be pivotable or slideable between its extended and retracted positions.

The signal acquisition device may include more than one temperature sensor for sensing temperature at different locations.

The temperature sensor may be used for measurement of the temperature of other items, for example for food, domestic heating systems or wine.

Electrical Sensor

The heart is triggered by electrical signals that can be detected on the skin, which is the basis of the electrocardiogram (ECG). A simple version of this can detect the time at which the electrical signal that initiates a heartbeat occurs by measuring the potential difference between two separated parts of the body. With appropriate electronic processing, the time of occurrence of each initiation signal can be measured to within a few milliseconds.

The signal acquisition device may include an electrical sensor comprising two electrodes which are electrically isolated from each other but which can be contacted by two different parts of a user's body. Preferably, the two electrodes can be contacted by one finger from each hand of the user. Preferably, one of the electrodes of the electrical sensor is associated with the button, pad or strap of the blood flow occlusion means (see below). The other electrode will be located on a separate part of the PHHM. That other electrode may be associated with a lever, if present, which is used for manual inflation of a pad (see below). Preferably the pad is constructed with a surface that gives a good electrical connection, such as an array of micro-pyramids.

Preferably, the signal which is acquired by the electrical sensor is a measure of the potential difference between the two electrodes, which is related to the potential difference between the two different body parts. Preferably, the processor of the PHHCD is adapted to amplify the signals from the electrical sensor and, if desired, to filter the signals before, during or after amplification. An amplified and filtered signal produced by the processor will generally have the form shown in FIG. 1 in the attached drawings where the x axis represents time and the y axis represents potential difference. The arrows in FIG. 1 indicate the time at which the electrical signal stimulates the heart to initiate systole.

Blood Flow Occlusion Means

The signal acquisition device may comprise a blood flow occlusion means for restricting or completely blocking the flow of blood through a part of a user's body and a pressure sensor for determining the pressure applied by or to the blood flow occlusion means. The conventional blood flow occlusion means is an inflatable cuff that surrounds the body part.

The signal acquisition device preferably includes one of the blood flow occlusion means that are described below: a button; a fluid-filled pad; and a strap. Any of these can be used by pressing it against a body part, such as a toe or finger, preferably a finger, where arterial blood flow through the body part is affected by pressure exerted on only one side of the body part, or vice versa.

The degree of occlusion may be detected by an oscillometric method or by analysis of the signals from a blood photosensor described below.

Button

The blood flow occlusion means may comprise a button that is pressed against the body part. Preferably, the button is a region of a plate, which region may move independently from the remainder of the plate and is connected to a force sensor. The force sensor is adapted to measure the force applied to the button but minimise the distance the button may move. Typically, the plate is of 10 mm by 20 mm with a circular button of typically 5 mm diameter or a non-circular button of similar area. Preferably, the distance the button moves when subject to the force of the body part is no more than 0.1 mm.

Pressing the button against the body part creates a pressure within the body part. The body part in contact with the button pushes against the button with a force approximately equal to the pressure within the body part multiplied by the area of the button. By measuring the force, the PHHM can make an accurate estimate of the pressure within the body part.

The signal acquisition device may include a plurality of buttons, each of which is connected to a separate force sensor.

Fluid-Filled Pad

The blood flow occlusion means may comprise a fluid-filled pad against which one side of a part of the user's body, in particular a digit, preferably a finger, can be pressed to occlude the flow of blood through that part of the body, and a pressure sensor for providing a signal indicative of the pressure in the pad. Preferably, the pad is located in a notch in the PHHM. In use, pressure may be applied to the pad either by pressing the body part onto the pad or by pressing the pad onto the body part.

If the pad is filled with air, it may be necessary to provide a means to prevent excess pressure occurring in the pad. This may arise, for example, if the device is left in a hot place and the heat causes the pressure to rise excessively. The excess pressure prevention means preferably includes a valve that opens to release gas from the pad to the atmosphere at a predetermined pressure, which is the maximum permitted pressure of the pad (typically around 300 mm Hg) and a pump for replacing the gas which has been released. The pump may comprise a piston and cylinder or it may comprise a diaphragm and chamber, and the piston or diaphragm may be operable by an action of the user or by electrical power. Preferably, the PHHM has a hinged or sliding cover over the signal acquisition device arranged such that, on opening the cover to allow the device to be used, the cover presses on the piston or diaphragm to create sufficient pressure to re-inflate the pad. Preferably, the pump has two valves: a one-way valve that allows gas to enter the pad; and a valve for opening to release gas from the pump to the atmosphere at a predetermined pressure, which is the minimum working pressure of the pad (typically around 50 mm Hg).

It is advantageous that the volume of gas present in the pad is minimised, to maximise the sensitivity of the detection of changes in pressure. If a one-way valve is used, it should preferably be located close to the pad and to the pressure sensor.

A further benefit of incorporating this prevention means is that the device continues to operate even if a slow leak develops. This will increase the reliability of the device.

Strap

In a further alternative, the blood flow occlusion means may comprise a strap against which one side of a part of the user's body, in particular a digit, preferably a finger, can be pressed to occlude the flow of blood through that part of the body, and a force sensor for providing a signal indicative of the pressure exerted on the strap.

Preferably, the strap is located in a notch in the PHHM. In use, pressure may be applied to the strap either by pressing the body part onto the strap or by pressing the strap onto the body part.

The strap may be inextensible or extensible.

Where the strap is inextensible, it may be fixedly mounted at each end across a notch in the PHHM. In this arrangement, the pressure sensor is adapted to measure the force applied to the strap's mountings.

Alternatively, an inextensible strap may be mounted on an axle at one side of a notch and fixedly mounted at the other side of the notch. In this arrangement, the pressure exerted on the strap may be measured by measuring the extent to which the strap has rolled around the axle. The unrolling may be resisted by a torque spring on the axle or a linear spring.

In a further alternative, an inextensible strap may be mounted at each of its ends on an axle and the axles are located at each end of a notch in the PHHM. In this arrangement, the pressure exerted on the strap may be measured by measuring the extent to which the strap has rolled around each axle or by measuring a physical property of the strap, such as its electrical resistance.

Where the strap is extensible, it may be fixedly mounted at each end across a notch in the PHHM. In this arrangement, the pressure sensor may be adapted to measure the increase in length of the strap or the tension in the strap or to measure a physical property of the strap, such as its electrical resistance, to provide the signal related to the pressure applied to the strap.

Where a strap is used, it is preferred that the PHHM includes means for providing a signal indicative of the diameter of the body part which comes into contact with the strap so that the pressure measurement can be made more accurate. The means may be a keypad or a touchscreen, advantageously the normal keypad or touchscreen of the PHHCD, by which a user may enter the diameter as measured by the user, for instance using any convenient means, such as a tape measure or a series of graduated cut-outs provided on a separate gauge or provided on the PHHM.

However, it is preferred that the means is associated with the strap itself and provides the signal without user input. For instance, the strap may include one or more optical fibres embedded therein, a light source at one end of the optical fibre(s) for injecting light into the optical fibre(s) and a light detector at the other end of optical fibre(s) for detecting the light reaching the detector and a means for determining the attenuation of the light as it passes through the optical fibre(s), the degree of attenuation being related to the curvature of the strap, which in turn is related to the diameter. Alternatively, the strap may comprise two layers and the signal acquisition device includes means for measuring the length of each layer, the relative lengths of the two layers being related to the diameter. In a further alternative, the signal acquisition device may include means, such as a proximity detector, for providing a signal indicative of the distance between the bottom of the notch and the closest point of the strap to the bottom of the notch and the processor is adapted to calculate the diameter of the body part based on the signal and the length of the strap.

Blood Photosensor for Photoplethysmography (PPG)

Pulse oximeters using PPG have been on the market since the 1980s. They are used to estimate the degree of oxygenation in arterial blood. Red and infra-red light is transmitted towards a body part. The infra-red light is more strongly absorbed by oxygenated blood than by non-oxygenated blood; red light is more strongly absorbed by non-oxygenated blood than by oxygenated blood. The change in the infra-red absorption during systole is a measure of the amount of oxygenated blood. The level of red light absorption between systoles is a measure of the total amount of blood being illuminated and is used for calibration.

Preferably, the signal acquisition device includes a PPG sensor. This uses one or more photosensors. The photosensor(s) may be arranged for transmission or scattering measurement. In transmission mode, the photosensor comprises one or more photo-emitters arranged to transmit light through the body part and one or more photo-detectors arranged to detect light transmitted from the photo-emitter(s) through that part. In scattering mode, the photosensor comprises one or more photo-emitters arranged to transmit light towards the body part and one or more photo-detectors arranged to detect light from the photo-emitter(s) scattered by the body part. Preferably, in scattering mode, the photo-detector(s) is(are) arranged in close proximity to the photo-emitter(s).

Preferably, in either case, the photosensor(s) is/are adapted to emit and detect light at two or more wavelengths. There may be a single, multiplexed photo-emitter adapted to emit light of two selected, different wavelengths or at least two photo-emitters, each of which is adapted to emit light of a selected, different wavelength. For either alternative of the photo-emitter(s), in one alternative, there is one multiplexed photo-detector which can detect light at the selected wavelengths. In another alternative, there are two or more photo-detectors, each of which is adapted to detect light of a selected, different wavelength.

Preferably, one of the wavelengths is chosen so that the light is absorbed more strongly by oxygenated blood than by deoxygenated blood. A suitable wavelength is 940 nm. Another wavelength is chosen so that the light is absorbed more strongly by deoxygenated blood than by oxygenated blood. A suitable wavelength is 660 nm.

Preferably, the signal acquisition device is adapted to acquire a signal from the photo-detector(s) when no light is emitted from the photo-emitter(s). This allows a further calibration of the signals obtained at the first and, if used, second wavelength(s).

FIG. 2 in the attached drawings shows schematically the variation in oxygenated blood signal (top line), deoxygenated blood signal (middle line) and ambient light signal (bottom line).

The blood photosensor may be further adapted to measure the concentration of analytes in the blood such as glucose, alcohol, haemoglobin, creatinine, cholesterol and stimulants or other drugs, including illegal or otherwise forbidden substances. These are difficult to measure if the absorption spectrum of the analyte is similar to that of other materials in the blood. The signal acquisition device may be designed to use one or more of the techniques described below to increase the sensitivity and selectivity of absorption spectroscopy.

The first technique is to use differential absorption. A beam of light is transmitted towards a body part and the transmitted or scattered light is split between two sensing cells. One (the reference cell) contains a mixture of the chemical species typically present in sufficient quantities in blood, excluding the analyte of interest. In practice this might only contain water. The other (the sample cell) contains the same mixture and the analyte. Alternatively, the reference cell may be omitted and the sample cell filled solely with the analyte. Alternatively, if the analyte can be gaseous under ambient conditions, the beam of light may pass through a single sample cell containing the analyte in gaseous form and the pressure in that cell is modulated.

The intensity of the beam of light may be measured under several conditions: after passing through the reference cell and separately after passing through the sample cell, in each case without the body part present, and similarly after passing though each cell with the body part present. Alternatively, the intensity of the beam of light may be measured both when it has passed through the cell and when it has not, again with the body part present and not. In another alternative, the intensity may be measured as a function of the pressure in the cell, with and without the body part present.

The intensity of the beam of light may be modulated, for example by switching, to allow the measurement system to compensate for ambient light. The beam of light has a broad optical spectrum chosen to maximise the discrimination between the analyte and other chemical species present whilst also allowing low cost technology to be employed. For example, if the analyte is glucose, this might be in the near IR region.

In each of these cases, the difference between the intensity when the beam of light has passed through the reference cell and through the sample cell is a measure of the amount of absorption by the analyte within the body part. In order further to improve the selectivity to the concentration of the analyte in blood, the PPG signal may be used to identify the time at which the artery dilates due to systole. The change in absorption at this point is a consequence solely of the additional amount of blood in the body part. The volume of that additional blood is also estimated from the PPG signal.

Acoustic Sensor

The PHHM may include an acoustic sensor for acquiring signals related to the sounds produced by the heartbeat. The acoustic sensor may be a separate microphone, geophone or vibration sensor or may be the microphone provided in a standard cellphone or tablet computer for speech reception or it may be the force or pressure sensor used to measure the pressure in the body part during arterial occlusion. Preferably the processor of the PHHM is adapted to process the signals acquired by the acoustic sensor to determine the time at which the heart beats.

FIG. 3 in the attached drawings shows a typical waveform of the "lub-dub" beat of the heart which would be acquired by the acoustic sensor. Two successive pulses are shown. The signal consists of an audio signal within an envelope of amplitude.

Movement Sensor

The PHHM may also include a movement sensor which is adapted to detect the location of the part of the user's body on which the signal acquisition device is located. Preferably, the processor of the PHHM is adapted to correlate the signal from the movement sensor with the signal from a pressure sensor to enable calibration of blood pressure measurement.

Preferably, the processor of the PHHM is adapted to issue instructions audibly or visibly to the user to move the body part so that such calibration can take place. The movement sensor may be an existing component of the PHHCD. It may detect inertial forces due to the acceleration of the PHHCD or pressure changes with altitude.

Ultrasonic Sensor

The signal acquisition device may include an ultrasonic sensor for forming an image of the cross-section of the artery and/or to use Doppler interferometry to estimate the flow velocity of the blood within the artery. Said ultrasonic sensor may consist of a set of individual elements that form an array.

Personal Data Entry Means

Preferably, the PHHM includes a personal data entry means and is adapted to store other personal data. The personal data entry means is preferably a keypad or touchscreen, advantageously the normal keypad or touchscreen of the PHHCD. The data which can be entered by these means may include but are not restricted to: height, weight, waist circumference, finger diameter and age.

Further Sensors and Means

The PHHM may further include means for applying electrical signals to the user's body and for detecting the signals produced in response to those signals, for instance to measure body properties such as body mass index.

The PHHM may include a sensor adapted to acquire signals from which the identity of the user can be derived, such as for taking a fingerprint of the user. This makes it possible to ensure that the derived measurements relating to the user's health can be associated directly to the user. Such an identity sensor may be associated with the pad of a blood flow occlusion means or may be associated with an electrode of an electrical sensor. It is possible to locate the identity sensor in such a way that it is almost impossible for the measured medical indicators to be of any person other than the identified user.

Data Analysis

The sensors and means described above may be used in various combinations to allow for the acquisition of various health-related data. The PHHM may include one or more of the temperature sensor, electrical sensor, blood flow occlusion means, blood photosensor for PPG, acoustic sensor, movement sensor, ultrasonic sensor and preferably includes at least the first four of these. Preferred combinations of sensors and means are set forth in the Table below, together with indications of the health-related data that may be derived using these combinations. However, it will be clear to the person skilled in the art that other combinations can be used to provide further health-related data and the present invention is not to be limited to the combinations set forth in the Table below.

| Health-related parameter | Measurement technique | | Relevant sensors | Notes | |
| --- | --- | --- | --- | --- | --- |
| Body temperature | Bolometry | | Temperature sensor | Bolometry is a mature technique. ThePHHM preferably uses feedback to guide the user to obtain the highest value (for example by moving around over the ear) and a model to extrapolate the changes as measured to estimate an asymptotic value and to correct for ambient. | |
| Pulse rate | Timing of pulses | | Electrical sensor Pressure sensor | The signal from the electrical sensor will be the most reliable and precisely timed. The signals from the two sensors will also be analysed to provide confirmation of the data and to improve accuracy. The analysis will, like that for blood pressure, seek the most likely value in the light of all of the available evidence. | |
| Pulse arrhythmia | Timing of pulses | | Blood photosensor | | |
| Blood pressure (systolic and diastolic) | Pulse Wave Transition Time (PWTT) | | Electrical sensor Blood photosensor Acoustic sensor Personal data | Pulse Wave Velocity (PWV) is a direct measure of blood pressure. The electrical sensor may be used to detect the time of initiation of the pulse. The acoustic sensor may be used when the user first calibrates the device to measure the time between electrical signal and start of systole. The PPG sensor may be used to detect the time at which the pulse reaches the finger. The personal data may be used to estimate the path length from heart to PPG sensor. | The actual blood pressure may be estimated by combining the five separate measurements (or as many as are available). The combination might not just be a simple average; the processing may seek to find the most likely value in the light of all available information, using a technique such as a Bayesian estimator to take account of all data including variations between pulses. |
| | Pulse volume | | Blood photosensor | The magnitude of the PPG signal is a measure of the change in arterial volume, which is related to blood pressure. | |
| | Sphygmomanometry (occlusion) | Pressure fluctuations | Pressure sensor | The applied pressure is measured by the pressure in the pad or the force on the strap or button. The blood flow rate can be detected by small changes in the pressure caused by changes in volume of the artery. | Both techniques may use feedback to guide the user to push harder or softer to map the pressure space. |
| | | Optical absorption | Pressure sensor Blood photosensor | The pulse volume depends on the external pressure, unaffected if it is less than diastoilc and falling to zero at systolic. | |
| | Timing of pulses | | As pulse rate | There is a correlation between pulse rate and blood pressure. Personal data, including records or previous measurements, will add to its relevance. | |

-continued

| Health-related parameter | Measurement technique | Relevant sensors | Notes | |
|---|---|---|---|---|
| Blood oxygen | PPG | Blood photosensor | Standard PPG technique, combining measurements of infra-red and visible absorption when the pulse reaches the finger. | |
| Pulse Wave Velocity | PWTT | | As above, in blood pressure measurement | |
| Respiration cycle | Effect on blood pressure and pulse | Blood photosensor | The respiration cycle is manifested in changes to the interval between pulses, the mean level of blood pressure and the magnitude of the PPG signal | The actual respiration cycle may be obtained by combining the four separate estimates (or as many as are available). |
| | | Electrical sensor | The respiration cycle is manifested in changes to the interval between pulses. | |
| Blood flow rate | Perturbation of respiratory cycle | Blood photosensor | The user may be instructed to hold his/her breath. The level of blood oxygen falls after the less oxygenated blood has reached the measurement point, and rises again after a breath is taken and the more oxygenated blood arrives | |

The Table does not refer to the analysis of the data derived from the possible extension of the optical sensor to measure the concentration of an analyte in the blood.

Algorithms relating the combination of signals from any or all of the sensors and means contained in the PHHM and from other sensors that may be part of the PHHCD may be used to convert the acquired signals to the relevant health-related data or improve the accuracy of the deduced medical indicators ("vital signs"), such as systolic and diastolic blood pressure. Other medical indicators that are less well-known but which are recognised by medical specialists, such as arterial wall stiffness and pulse arrhythmia, may also be extracted. Any or all of these models may be coded as software and can be loaded onto the PHHM or onto a remote computer for processing of the signals.

Preferably, the processor of the PHHM is adapted to provide audible or visual instructions to the user to enable the user to use the PHHM optimally. In this case, it is preferred that the processor is adapted so that the instructions are interactive and based on signals received from the signal acquisition device, which can be used to determine whether the signal acquisition device is in the best position or being used correctly.

It is preferred that the processor is adapted to take multiple measurements and correlate all those measurements to provide a better indication of the health data. One possible arrangement by which the data from the sensors is analysed is described after the Table.

Body Temperature

The accuracy of the estimate of core temperature can be improved by adapting the processor of the PHHCD to provide audible or visual feedback for instructing the user to move the PHHM so as to give the maximum temperature reading, for example when the PHHM is against the user's ear and is moved to ensure that the sensor is directed to the warmest place.

Preferably, the temperature sensor is positioned in the PHHM so that the PHHM is able to cover the body part whose temperature is being measured, such as the ear. In this case, in use, the temperature may rise towards core temperature because drafts are excluded by the presence of the PHHM. The temperature sensor may be collocated or combined with a loudspeaker or other device used to reproduce sound in the PHHCD.

Preferably, the processor is adapted to record the measured temperature over a period of several seconds and to use a mathematical model to extrapolate to an expected equilibrium temperature.

The processor of the PHHM may be adapted to analyse the signals from the temperature sensor to provide an estimate of the core body temperature of the user. The processor may be further adapted to carry out analysis to identify trends in core temperature and other derived information of diagnostic value.

Pulse Rate

The time of each pulse may be determined from the electrical signal, which indicates initiation of the systole, and also from the time of arrival of the systolic pulse at the body part against which the device is pressed, indicated by the pressure on the pressure or force sensor in the occlusion means and by the absorption peak detected by the optical sensor and/or by the acoustic sensor, if present.

The average pulse rate most compatible with all of the data from each of those sensors is found by means of an optimising mathematical algorithm which the processor of the PHHCD is adapted to operate. This may be a simple least-squares difference calculation with weighting or may use a Bayesian estimator or other optimising technique to find the most likely estimate.

Pulse Arrhythmia

Arrhythmia is a term used to refer to the variation of the interval between pulses. The patterns of such variations are a valuable diagnostic tool.

The variations may be obtained from the same data as is used to find the average pulse rate, again optionally using an optimising mathematical algorithm.

Blood Pressure

Blood pressure may be estimated by combining the data from four different types of evidence: pulse wave velocity, pulse volume, sphygmomanometry and pulse rate. Sphygmomanometry is itself derived from two different measurements, from the high frequency signals from the pressure sensor and from the blood photosensor(s). External data, such as height, weight, age and sex of the user, may also be exploited. There are thus five separate measurements and several pieces of data that may be combined using an optimising mathematical algorithm such as a Bayesian estimator to obtain the most reliable estimate of blood pressure.

The resulting values are the systolic and diastolic blood pressure at the location of the body part at which the measurement was made. Other diagnostic information may be extracted from the signals by means of further mathematical models. For example, the analysis may calculate the blood pressure at another point on the body, such as the upper arm so as to allow direct comparison with the measurements by a conventional cuff-based sphygmomanometer. It may also calculate pressure at the aorta and also arterial stiffness.

Optionally the PHHM may include a further temperature sensor to detect the artery to be tested.

Each of the measurements of blood pressure is described below.

Pulse Wave Velocity

Pulse wave velocity (PWV) may be derived from pulse wave transition time (PWTT).

The use of PWV to estimate blood pressure (BP) is described in detail by Padilla et al. (Padilla J et al., "Pulse Wave Velocity and digital volume pulse as indirect estimators of blood pressure: pilot study on healthy volunteers" Cardiovasc. Eng. (2009) 9:104-112), which in turn references earlier work on a similar subject from 1995 and its specific use for estimating of BP in 2000. The technique is described in U.S. Pat. No. 5,865,755 dated Feb. 2, 1999. It relies on the observation that the speed at which a blood pulse travels along the arteries is a function of the arterial blood pressure.

Preferably, the processor of the PHHM is adapted to derive an estimate of PWV from the signals obtained from the electrical sensor and the PPG sensor. The processor is adapted to process the signal from the electrical sensor to provide an indication of the time at which systole (the heart beat) is initiated and to process the signal from the photosensor to determine time of occurrence of the peak in the oxygenated signal, which indicates the time at which the pulse reaches the measurement point. The interval between these is a measure of the time taken for the pulse to travel from the heart to the measurement point (the PWTT). The processor is adapted to determine the BP in relation to this interval, which is typically 300 ms for measurements at the end of the wrist or hand.

Preferably, the processor is adapted to make use of two further pieces of information to estimate PWV: the time delay between the electrical initiation signal and the initiation of systole by the heart; and the length of the path between the heart and the measurement point.

Preferably, the processor is adapted to analyse the acoustic signal to extract the envelope (analogous to detection in radio signals) and to use a threshold set automatically to identify the point that indicates the initiation of systole. In practice, this could be at a defined fraction of the change from background and peak, as shown in FIG. 4 of the attached drawings, where the vertical arrows indicate the time at which the heart responds to a physiological electrical initiation signal and initiates systole. This is typically a few tens of milliseconds after the electrical initiation signal. Alternatively, the processor is adapted to match a curve to the waveform to make a more robust estimate.

Alternatively, the time delay may be estimated by measuring the PWTT to two different parts of the body, such as the carotid artery and the finger. The time delay can then be found from knowledge of the typical ratio of the path lengths from the heart to the two different parts of the body.

Preferably, the PHHM is adapted to store the time delay in non-volatile memory. It may be stored automatically when measured or entered into memory by user input using a keypad or touchscreen, advantageously the normal keypad or touchscreen of the PHHCD.

Preferably, the PHHM is adapted to store in non-volatile memory a value related to the length of the path between the heart and the measuring point. It may be entered into memory by user input using a keypad or touchscreen. The value entered may be an exact measure of the length or may be a value which is approximately proportional to the actual length, such as the user's height.

Pulse Volume

Pulse volume may be derived from the blood photosensor (PPG). The use of PPG for estimating BP was reported by X. F. Teng and Y. T. Zhang at the IEEE EMBS, Cancun, Mexico, Sep. 17-21, 2003. The basic technique was the subject of U.S. Pat. No. 5,140,990, dated Aug. 25, 1992. The change of the infra-red absorption during systole is a measure of the change in volume of the artery being illuminated, which is related to the pressure within the artery.

Further data may be derived from analysis of the shape of the absorption peak during systole, such as analysis of the total area under the peak.

Preferably, for the signal for oxygenated blood, the processor of the PHHM is adapted to derive properties of the blood flow such as the relative amplitude and timing of the direct and reflected pressure wave from the shape of the curve such as from the area under the peak, its width at half-height and the height and width of the shoulder. Optionally, the processor of the PHHM may be adapted to calculate ratios of these to reduce the effect of variations in illumination and location relative to the body part. These ratios may be used to characterise the properties of the blood flow.

The processor of the PHHM is preferably adapted to analyse the signals from the PPG sensor to provide a direct estimate of systolic and diastolic blood pressure at the point of measurement.

Sphygmomanometry (Arterial Occlusion)

Sphygmomanometry is a mature technique for measuring BP which has been in use for more than 100 years. Variable external pressure is applied with a cuff around the body part within which an artery runs. The pressure reduces the cross-section of the artery and restricts the flow of blood during systole.

Sphygmomanometry is conventionally conducted with a cuff that surrounds the body part and is inflated to a pressure at which all blood flow is stopped; the pressure is then slowly released. Systolic BP is measured by finding the smallest pressure that completely occludes the flow. Diastolic BP is measured by finding the largest pressure that does not cause any occlusion. The flow traditionally is detected by a skilled practitioner using a stethoscope to hear the sounds of the blood flowing (Korotkoff sounds).

Automatic sphygmomanometers detect the flow either by detecting fluctuations in pressure in the cuff caused by the flow (oscillometric method, see, for example, the Freescale Application Note AN1571, "Digital Blood Pressure Meter") or by optically sensing small movements of the skin. The magnitude of those fluctuations is an indicator of the degree of occlusion. More recently, PPG has been used by combining sphygmomanometry with the measurement of pulse volume (see Reisner et al., "Utility of the Photoplethysmogram in Circulatory Monitoring" Anesthesiology 2008; 108: 950-8).

The signal acquisition device may use any one of the three means of occlusion described above: a fluid-filled pad, a strap or a button. It uses both the pressure fluctuations and the measurement of pulse volume to determine the systolic and diastolic pressures.

Unlike conventional sphygmomanometry, flow may be detected at a range of pressures in any order and the data fitted to a known mathematical equation. It is preferred that the processor is adapted to issue audible or visual instructions to the user to vary the force applied to the body part to cover a wide enough range of pressures to give a good fit to that mathematical equation. For instance, if the user has not pressed hard enough against the button, strap or pad referred to above to occlude completely a blood vessel during a systole, the device may be programmed to issue an instruction to the user to press harder on the occlusion means (or vice versa) so that the required data can be acquired.

This capability allows the pressure applied to the occlusion means to be apparently random. In carrying out blood pressure monitoring, the user may vary the pressure applied to the button, pad or strap referred to above in a random manner. However, the data from the blood flow sensor can be correlated with the signal from the pressure sensor of the button, pad or strap to fit the measured data to a known theoretical relationship between flow rate and pressure (see, for example, the model shown on page 954 of Reisner ("Utility of the Photoplethysmogram in Circulatory Monitoring" Anesthesiology 2008; 108:950-8)).

Pulse Rate

Pulse rate may be measured separately and can be used as an indicator of blood pressure. Al Jaafreh ("New model to estimate mean blood pressure by heart rate with stroke volume changing influence", Proc 28th IEEE EMBS Annual Intnl Conf 2006) concludes that: "The relationship between heart rate (HR) and mean blood pressure (MBP) is nonlinear". The paper then shows how allowance for stroke volume can compensate for some of that non-linearity. Stroke volume is estimated separately (see below) and personal data may also be used.

Blood Oxygen

The blood photosensor can use PPG to estimate blood oxygen levels. At least four variables may be derived from the measured absorption at two wavelengths. These are the amplitude of the detected signal at each wavelength at systole and between systoles. The arrow in FIG. 2 shows one of the values that may be derived from these, the height of the peak corresponding to the change in oxygenated blood signal at systole. It is established that these four values may be analysed to estimate the oxygenation of the blood (see for example Azmal et al., "Continuous Measurement of Oxygen Saturation Level using Photoplethysmography signal", Intl, Conf. on Biomedical and Pharmaceutical Engineering 2006, 504-7).

Pulse Wave Velocity

The pulse wave transition time may be measured as set out above and converted into an estimate of Pulse Wave Velocity. This information is of direct diagnostic value to a skilled medical practitioner, especially if considered with all the other data obtainable from the signal acquisition device of the present invention.

Respiration Cycle

The state of the respiration cycle may be detected from several of the data sets measurable by the present invention:
  pulse rate (measured by electrical sensor and blood photosensor, see above);
  mean blood pressure (see above); and
  amplitude of the systolic pulse (measured by PPG, see above).

The results of all of these measurements may be combined using an optimising mathematical algorithm such as a Bayesian estimator to obtain the most reliable description of the amplitude and phase of the respiratory cycle.

Blood Flow Rate/Heart Stroke Volume

The volume pumped by the heart on each pulse is conventionally measured using an ultrasound scan. The cross-sectional area of the aorta is estimated from the image and the flow rate from the Doppler shift. This is a mature and inexpensive technique but is only available at the doctor's office.

Before ultrasound was readily available, a convenient and almost non-invasive technique was to estimate the time taken for blood to circulate around the body. This is related to the pulse rate and the volume pumped on each pulse. The technique used a strong-tasting but harmless chemical that was injected into a vein in the arm and the time measured before it reached the patient's tongue and could be tasted.

The present invention allows a similar measurement to be made by perturbing the respiratory cycle. The PHHCD may be adapted to instruct the user to hold his/her breath. The level of oxygen in the lungs starts to fall and the oxygenation of the blood in the lungs falls with it. Once this blood reaches the body point at which measurements are being made, the blood oxygen level will be seen to fall. The time interval, when combined with assumed or entered data as to the path length, is a measure of flow velocity. The PHHCD then instructs the user to start breathing again and the time taken for the blood oxygen level to start to rise again may also be measured.

Remote Data Processing

The PHHM is capable of making and displaying measurements of any or any combination or all of the "vital signs" listed above without any external data processing. Additional features and improved accuracy may be provided by external data processing, using the communications capability of the PHHCD to connect to the Internet, a cellular telephone network or other communications means.

Preferably, each PHHM according to the invention has a unique, unalterable, electronically-readable identifier. This may be provided during manufacture or testing. Furthermore, each PHHM preferably includes circuitry to encrypt the measured data in a manner that is unique to that device.

In one embodiment of the present invention, the PHHCD reads the unique identifier when the PHHM is first used and transmits that identifier to a remote secure data service (RSDS) by means of the Internet. The RSDS downloads to the PHHCD the necessary software, calibration data and decryption key to extract the data from the PHHM. This is a more reliable way of ensuring the proper calibration of the signal acquisition device and minimises the time required for installation and final test of the PHHM into the PHHCD. The PHHCD is preferably further programmed to communicate the measured data directly to the user, for instance via a visual display or audibly. Preferably, the communication is via a visual display. If desired, the processor may be programmed so that the display shows not only the measured parameter(s) but also trends in the measured parameter(s).

Optionally, the software may be time-limited, requiring the user to revalidate it with the RSDS after a fixed period of time. Optionally, the user may be required to pay a licence fee for some or all of the capability to be enabled.

Alternatively, the decryption key and calibration data may be retained by the RSDS. The PHHCD transmits the encrypted raw data from the PHHM to the RSDS for analysis. The RSDS then returns the decrypted, calibrated data for further processing and display to the user The RSDS may carry out further processing of the measured data to obtain greater accuracy or to derive further diagnostic or indicative data. These data may be retransmitted to the PHHCD for display to the user.

The PHHCD may also be programmed by the RSDS to transmit the acquired signals or the derived measurements to a remote location, for instance a user's, clinician's, health care provider's or insurance company's computer system where the acquired signals or measurements may be processed remotely, for instance to provide a more accurate analysis, or for the results of the analysis to be interpreted either automatically or by a skilled doctor. If the processor is so programmed, it may also be programmed to receive the results of such analysis and display such results to the user, as described above.

The PHHCD may also be programmed by the RSDS to permit third party applications (commonly known as "apps") access to the data from the PHHM. Such permission may be made subject to the payment of a licence fee or to the app having been endorsed by the relevant regulatory authorities.

The PHHCD may also be programmed to provide information related to the derived measurement(s), such a normal ranges or recommendations for action.

The RSDS can offer a service to store many measurements from a PHHM and analyse trends and other derived information for the user. This may be linked to an automatic alert service in the event of any significant changes in the data. In addition, the signals or measurements can be anonymized and gathered from groups of or all PHHMs of the invention so that they can be used for research purposes.

Physical Construction

A number of different sensors and means, as referred to above, can be incorporated into the PHHM. They can be incorporated individually or in any combination of two or more sensors. For instance, a combination of a sensor for measuring the pressure applied by a pad, strap or button, or applied to a pad, strap or button, a photosensor for measuring blood flow in a body part to which the pressure is applied and an electrical sensor for measuring pulse rate is particularly useful for providing more accurate data for determining blood pressure. Preferably, the PHHM integrates one or more Application Specific Integrated Circuits (ASIC), one or more Micro-Engineered Measurement Systems (MEMS) and/or photo-emitters and/or photo-detectors. They may be integrated as separate silicon devices in a single package or, preferably, some or all of them may be incorporated on one or more silicon devices. Such integration will bring several benefits, included reduced cost, improved reliability, reduced size and mass and reduced power consumption.

Preferably the PHHM exploits the other capabilities of PHHCD for calibration and operation.

Four embodiments of the present invention will now be described by way of example only with reference to the accompanying drawings, in which:

FIG. 1 shows a generalised amplified and filtered signal acquired by an electrical sensor;

FIG. 2 shows schematically the variation in oxygenated blood signal (top line), deoxygenated blood signal (middle line) and ambient light signal (bottom line) acquired from a PPG sensor;

FIG. 3 shows a typical signal waveform of the "lub-dub" beat of a heart acquired by an acoustic sensor;

FIG. 4 shows the envelope derived from the acoustic signal of FIG. 3;

FIG. 6 is a schematic illustration of a second embodiment of the present invention;

FIG. 7 is a schematic illustration of a third embodiment of the present invention;

It should be clearly understood that the following description of these three embodiments is provided purely by way of illustration and that the scope of the invention is not limited to this description; rather the scope of the invention is set out in the attached claims.

Figure 5:
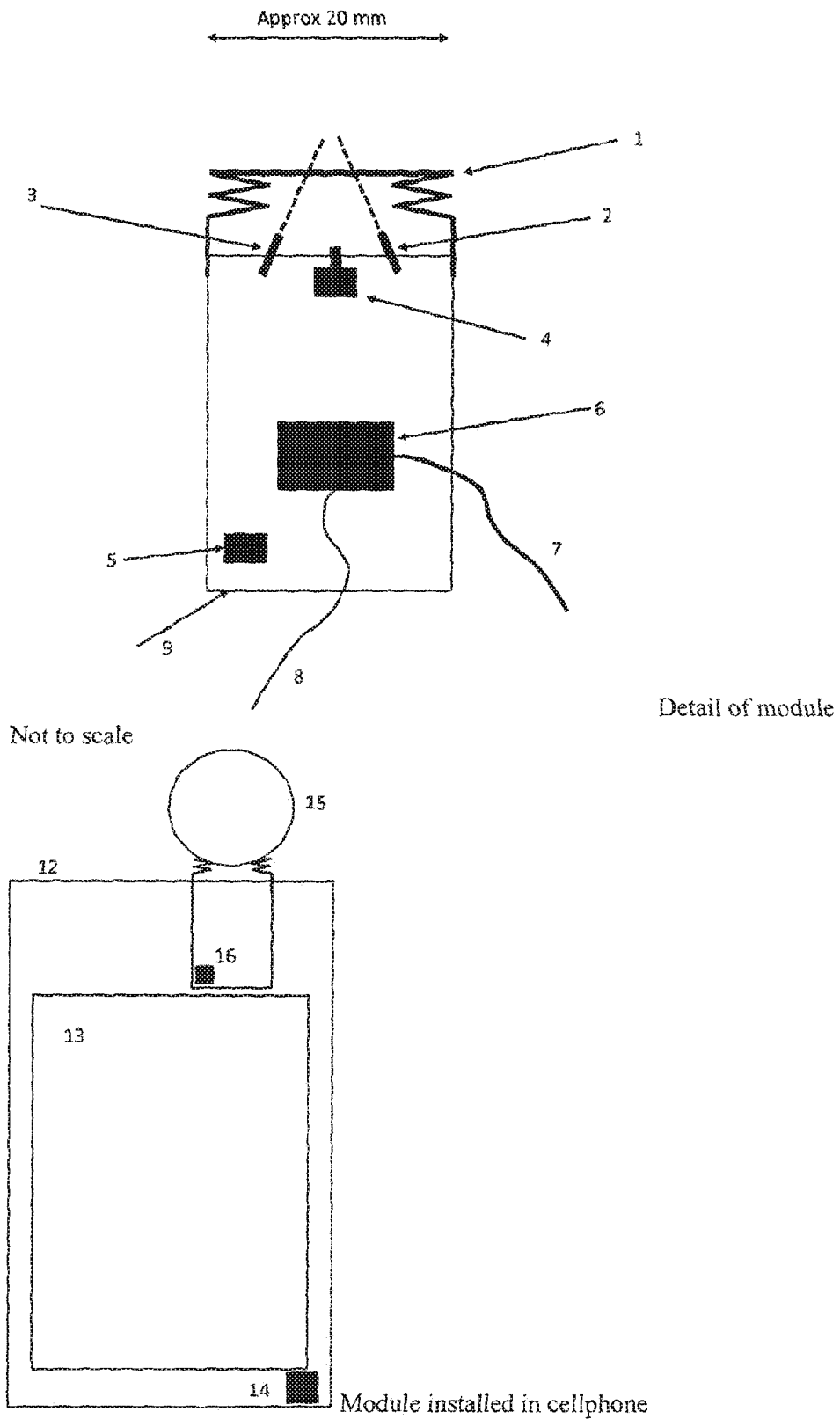
FIG. 5 is a schematic illustration of a first embodiment of the present invention.

FIG. 5 shows the detail of a module that is one embodiment of the invention and the module installed in a cellphone. There is a flexible bellows (1) sealed onto the end of the module case (9). The bellows (1) is filled with an inert transparent liquid. The bellows is transparent in the centre and, around the transparent region, is metallised to make electrical contact with a finger. The metallisation may use micropyramids or other rough structures to improve the electrical contact.

One or more photo-emitters (2) transmit light (shown by the dotted line) through the bellows (1). One or more photo-sensors (3) detect the light scattered back from a finger (15) pressed on the bellows (1).

A pressure sensor (4) measures the pressure in the liquid. A temperature sensor (5) detects the temperature of any object in its field of view, which is above the module.

The metallisation, photo-emitter(s), photo-sensor(s), pressure sensor and temperature sensor are all connected to a control and interfacing electronic unit (6). A cable (7) from this unit connects to the cellphone processor using the I2C interface standard. A second cable (8) connects this unit to a pad (12) on the cellphone used to make electrical contact to another finger.

The photo-emitter(s), photo-sensor(s), pressure sensor, temperature sensor and electronic unit may be separate silicon chips or some or all of them may be combined into a single chip.

The module is located at the top of the cellphone casing (12), above the screen (11). A pad (14) for connecting to a finger of the other hand is located at the bottom of the cellphone case. The user presses his/her index finger (15) against the bellows (1) to make a measurement. The temperature sensor is behind a window (16).

FIG. 6 shows the detail of a second module that is another embodiment of the invention and the module installed in a cellphone. There is an inextensible strap (21) attached to the module body (29). The surface of the strap is metallised to make electrical contact with a finger of a user.

One or more photo-emitters (22) transmits light (shown by the dotted line) beside the strap. One or more photo-sensors (23) detect the light scattered back from the finger.

There is a slot (24) in the body, below the point at which one end of the strap is attached. The beam formed by this slot deforms when force is applied to the strap and the deformation is measured by a strain gauge (25). A proximity sensor (31) measures the distance from the strap to the module body. A temperature sensor (26) detects the temperature of any object in its field of view, which is above the module.

The metallisation, photo-emitter(s), photo-sensor(s), strain gauge, proximity sensor and temperature sensor are all connected to a control and interfacing electronic unit (30). A cable (27) from this unit connects to the cellphone processor using the I2C or another interface standard. A second cable

(28) connects this unit to a pad (34) on the cellphone used to make electrical contact to a finger on the user's other hand.

The photo-emitter(s), photo-sensor(s), proximity sensor, strain gauge temperature sensor and electronic unit may be separate silicon chips or some or all of them may be combined into a single chip.

The module is located at the top of the cellphone casing (32), above the screen (33). The pad (34) for connecting to a finger of the other hand is located at the bottom of the cellphone case. The user presses his index finger (35) against the strap to make a measurement. The temperature sensor is behind a window (36).

FIG. 7 shows the detail of a third module that is another embodiment of the invention and installation in the cellphone. There is an extensible strap (41) that is attaché at one end to the module body (49) and at the other end passes over a roller (45) to a spring (44). Within the spring (not shown) is a sensor to measure its length. The surface of the strap is metallised to make electrical contact with a finger.

One or more photo-emitters (42) transmit light (shown by the dotted line) beside the strap. One or more photo-sensors (43) detect the light scattered back from the finger.

A proximity sensor (51) measures the distance from the strap to the module body. A temperature sensor (46) detects the temperature of any object in its field of view, which is above the module.

The metallisation, photo-emitter(s), photo-sensor(s), spring length sensor, proximity sensor and temperature sensor are all connected to a control and interfacing electronic unit (50). A cable (47) from this unit connects to the cellphone processor using the I2C or another interface standard. A second cable (48) connects this unit to a pad (54) on the cellphone used to make electrical contact to a finger on the user's other hand.

The photo-emitter(s), photo-sensor(s), proximity sensor, spring length sensor, temperature sensor and electronic unit may be separate silicon chips or some or all of them may be combined into a single chip.

The module is located at the top of the cellphone casing (52), above the screen (53). The pad (54) for connecting to a finger of the other hand is located at the bottom of the cellphone casing. The user presses his/her index finger (55) against the strap to make a measurement. The temperature sensor is behind a window (56).

Figure 8:
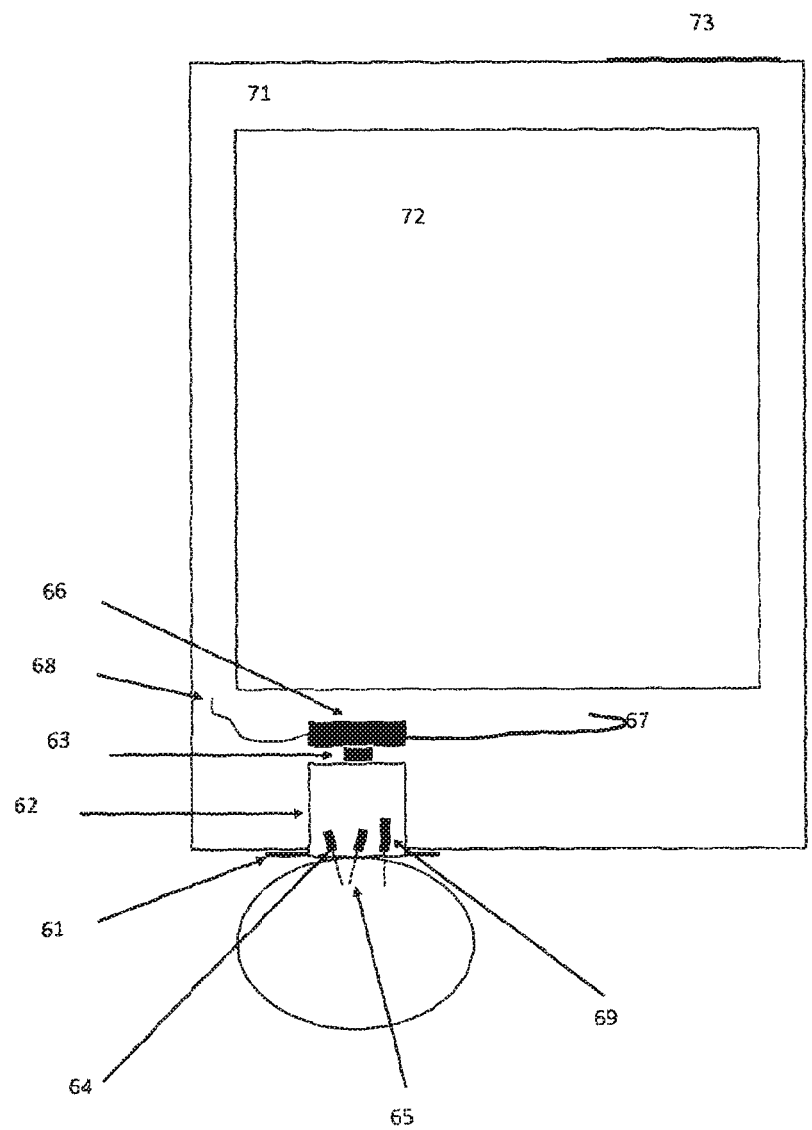
FIG. 8 is a schematic illustration of a fourth embodiment of the present invention.

FIG. 8 shows the detail of a fourth module that is another embodiment of the invention and installation in the cellphone. There is a plate (61) into which a button (62) is inserted so that the top of the button (62) is flush with the plate. The button (62) rests on a force sensor (63). One or more photo-emitters (64) transmit light (shown by the dotted line) through the top of the button (62). One or more photo-sensors (65) detect the light scattered back from a finger pressed onto the button (62). The top of the button (62) is metallised (not shown).

The metallisation, photo-emitter(s), photo-sensor(s), and force sensor are all connected to a control and interfacing electronic unit (66). A cable (67) from this unit connects to the cellphone processor using the I2C or another interface standard. A second cable (68) connects this unit to a pad (73) on the cellphone used to make electrical contact to a finger on the user's other hand.

For calibration, the PHHCD may be oriented by the user to be pointing upwards or downwards and the orientation may be detected using the PHHCD's existing sensors. The change in signal of the force sensor under the weight of the button in these two orientations may be used to calibrate the force sensor.

A temperature sensor (69) may also be contained within the button (62) or located separately and connected to the button (62). The module is located at the bottom of the cellphone casing (71), below the screen (72). The pad (73) for connecting to a finger of the other hand is located at the top of the cellphone casing.

Figure 9:
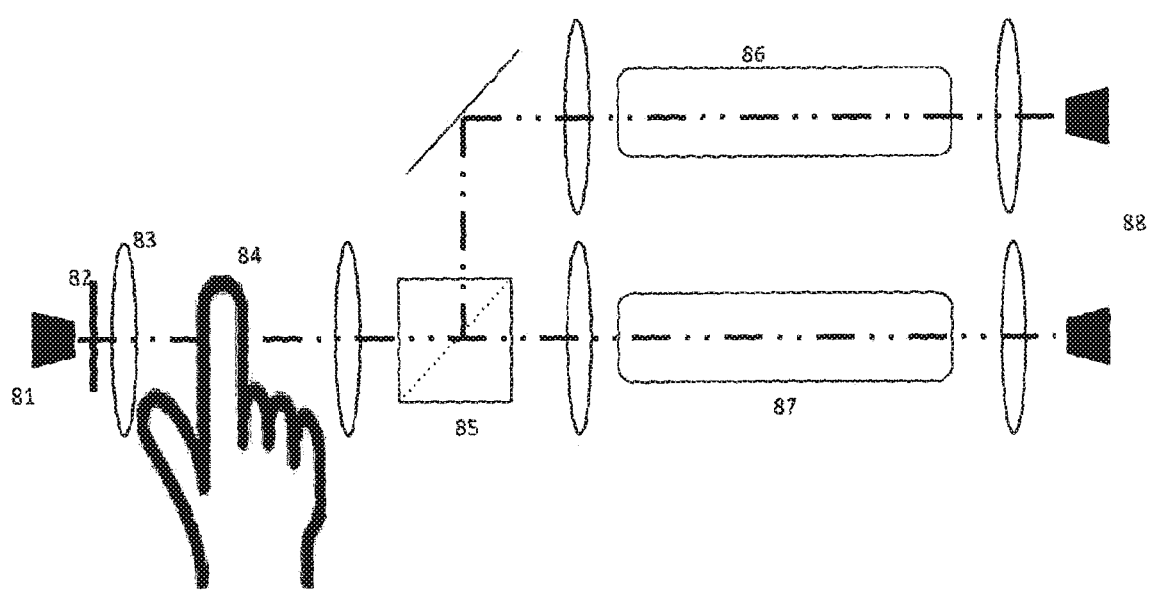
FIGS. 9, 10 and 11 each shows an arrangement for an optical sensor to be used in a PHHM of the present invention.
Figure 10:
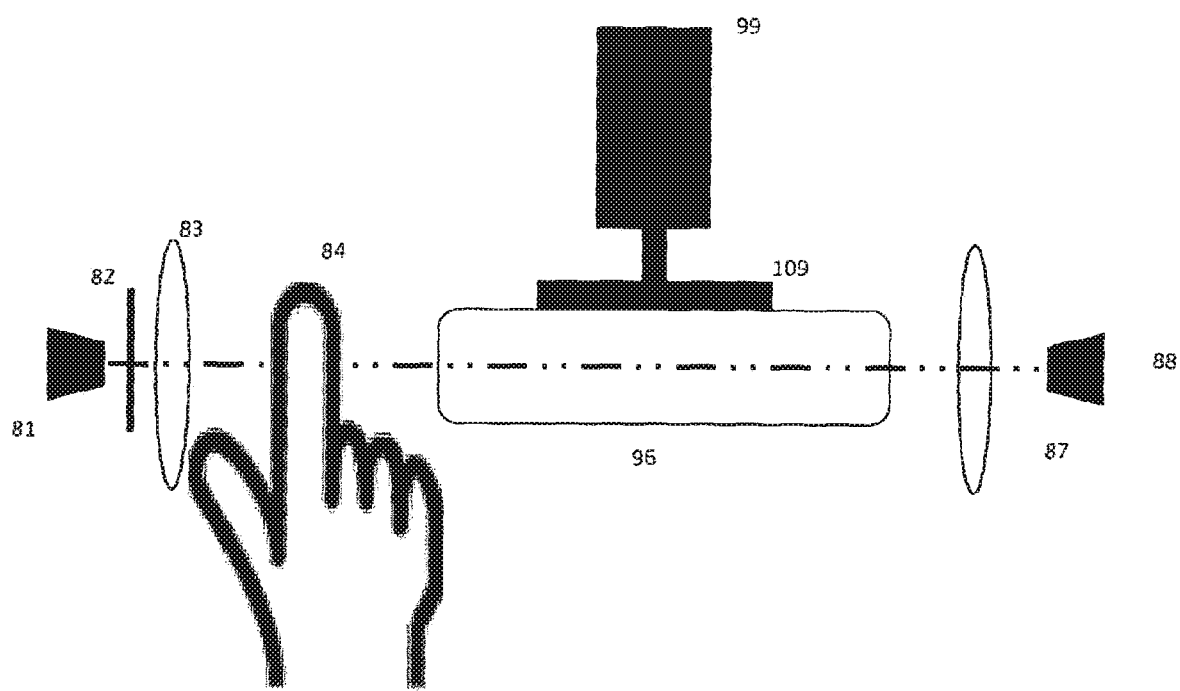
Figure 11:
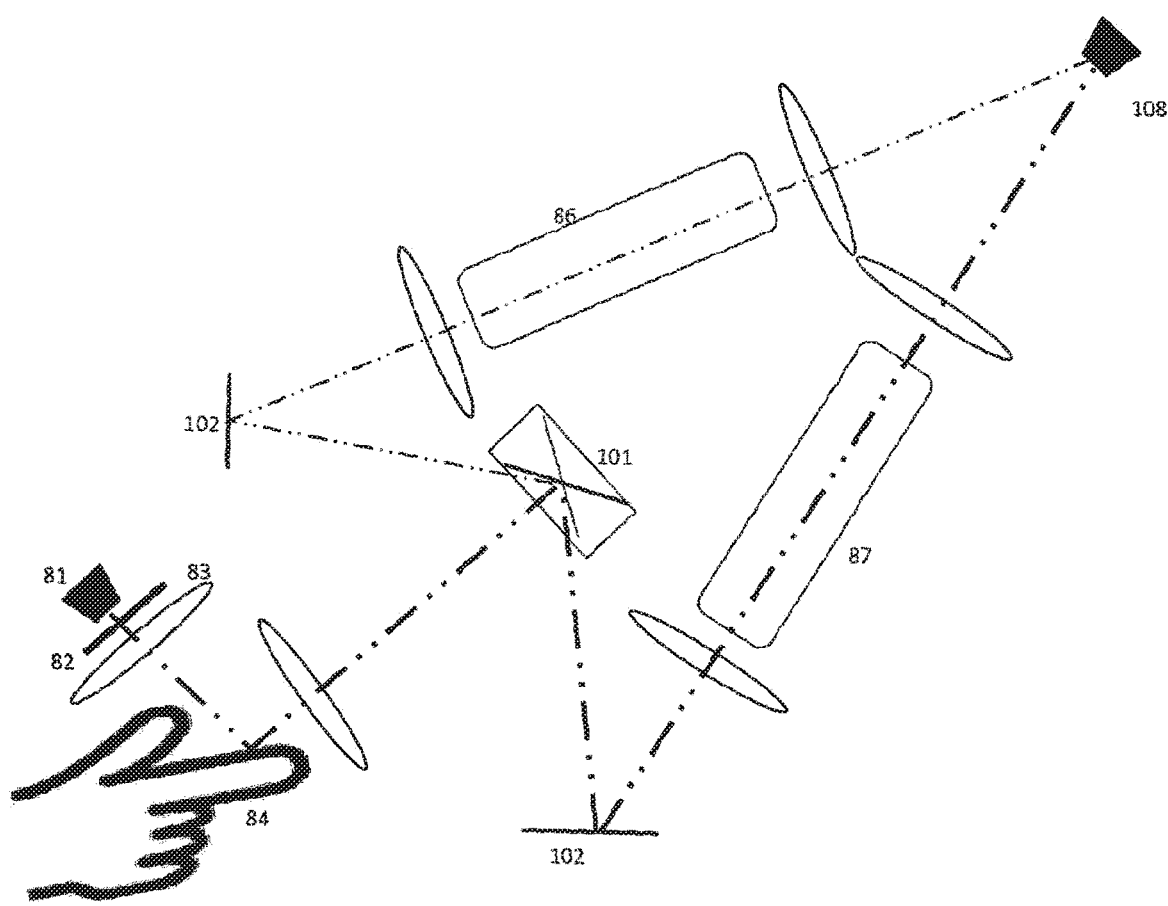

FIGS. 9, 10 and 11 show three arrangements of optical sensors to be used in the PHHM of the present invention to measure the concentration of an analyte in blood. This may be incorporated into a PHHCD, or may be connected to a PHHCD, or may be constructed as a stand-alone device with its own user interface, power supply and other electronic and mechanical components. Not shown is the photoplethysmography means or the mechanism to modulate the intensity of the light beam. The three illustrations show discrete optical and other components; alternatively the sensor might be implemented as one or more integrated optical devices where several optical components are formed in a single block of transparent plastic.

In FIG. 9, the light source (81) transmits a beam of light that passes through a filter (82) to select the spectral band of the light to be used. The spectral band is chosen to allow inexpensive components and materials to be used whilst maximising the sensitivity and discrimination with respect to the analyte. The beam is collimated by a lens (83) to shine through a body part such as finger (84). A beam splitter (85) divides the beam between a reference cell (86) and sample cell (87). Photosensors (88) measure the intensity of the beam after it has passed through each cell. A differential amplifier may be used to amplify the difference in signal between the two photosensors.

FIG. 10 shows another implementation in which a sample cell (96) containing gaseous analyte has one or more walls forming a diaphragm (109) moved by an actuator (99).

FIG. 11 shows another implementation in which the light source and detectors are on the same side of a body part, the detectors being sensitive to the light scattered back from the body part. A moving mirror (101) reflects light sequentially to each of two fixed mirrors (102) and hence to the reference cell or sample cell. One or more photosensors (108) measures the intensity of the beam that has passed the cells.

All of the illustrated embodiments of the PHHM include one or more electronic components (not shown) that can include: one or more pressure sensors, one or more analogue to digital convertors, one or more temperature sensors, a unique identifier and an interface to the electronic circuits of the cellphone.

The invention claimed is:

1. A personal hand-held monitor comprising:
   a processor,
   a signal acquisition device configured to acquire signals which can be used by the processor to derive a blood pressure measurement of a user, the signal acquisition device being integrated with a personal hand-held computing device, wherein the signal acquisition device comprises a blood flow occlusion device configured to be pressed against one side only of a body part or to have one side only of the body part pressed against it such that pressures are applied by the blood flow occlusion device to the body part or by the body part to the blood flow occlusion device, a pressure sensor configured to measure the pressures that are applied by the blood flow occlusion device to the body part or by the body part to the blood flow occlusion device, a blood flow detecting device configured to detect flow of blood through the body part, wherein the processor is configured to determine a measurement of blood pressure from the applied pressures and the detected flow of blood when the applied pressures are applied in an order that does not generally increase or generally decrease or generally increase then generally decrease.

2. The personal hand-held monitor of claim 1, wherein the blood flow detecting device employs an oscillometric method.

3. The personal hand-held monitor of claim 1, wherein the blood flow detecting device is an optical sensor.

4. The personal hand-held monitor of claim 1, which is adapted to provide audible or visual instructions to the user to adjust the force with which the blood flow occlusion device is pressed on the body part or with which the body part is pressed onto the blood flow occlusion device in response to signals from the personal hand-held monitor so as to ensure that measurements are made at a sufficient range of applied forces to allow the estimation of systolic and diastolic blood pressure.

5. The personal hand-held monitor of claim 1, wherein the blood flow occlusion device comprises a pad filled with a fluid and the pressure sensor for measuring the pressure determines the pressure in the fluid.

6. The personal hand-held monitor of claim 1, wherein the processor of the personal hand-held monitor is adapted to estimate systolic and diastolic blood pressure by relating blood flow to the applied pressures.

7. The personal hand-held monitor of claim 1, wherein the blood flow occlusion device is configured to, in use, at least partially occlude the blood flow.

8. The personal hand-held monitor of claim 1, wherein an entirety of the blood flow occlusion device is adapted to be pressed against one side only of the body part or to have one side only of the body part pressed against it.

9. The personal hand-held monitor of claim 1, wherein the processor is configured to fit the flow at the range of the applied pressures to a mathematical equation to determine the measurement of blood pressure.

10. The personal hand-held monitor of claim 1, wherein the processor is configured to correlate the detected flow of blood with the applied pressures to fit the detected flow to a theoretical relationship between flow and pressure.

11. The personal hand-held monitor of claim 1, wherein the personal hand-held monitor is configured such that the user manually varies force applied by the blood flow occlusion device to the body part or by the body part to the blood flow occlusion device.

12. The personal hand-held monitor of claim 1, wherein the blood flow occlusion device is configured such that the pressure is applied by a person pressing the blood flow occlusion device against the body part or pressing the body part against the blood flow occlusion device.

13. The personal hand-held monitor of claim 12, wherein the personal hand-held monitor is configured to determine the measurement of the blood pressure as a person presses the blood flow occlusion device against the body part or presses the body part against the blood flow occlusion device.

14. The personal hand-held monitor of claim 1, wherein the personal hand-held monitor is configured to determine the measurement of blood pressure without applied pressure being applied to another side of the body part, opposite the one side.

15. The personal hand-held monitor of claim 1, wherein the personal-hand held computing device is a cellphone, a tablet computer, or a personal digital assistant (PDA).

16. A personal hand-held monitor comprising:
a processor,
a signal acquisition device configured to acquire signals which can be used by the processor to derive a blood pressure measurement of a user, the signal acquisition device being integrated with a cellphone, a tablet computer, or a personal digital assistant (PDA), wherein the signal acquisition device comprises a fluid-filled pad configured to be pressed against one side only of a body part or to have one side only of the body part pressed against it such that pressures are applied by the fluid-filled pad to the body part or by the body part to the fluid-filled pad,
a pressure sensor configured to measure the pressures that are applied by the fluid-filled pad to the body part or by the body part to the fluid-filled pad,
an optical sensor configured to detect flow of blood through the body part, wherein the processor is configured to determine a measurement of blood pressure from the applied pressures and the detected flow of blood when the applied pressures are applied in an order that does not generally increase or generally decrease or generally increase then generally decrease.

17. A personal hand-held monitor comprising:
a processor,
a signal acquisition device configured to acquire signals which can be used by the processor to derive a blood pressure measurement of a user, the signal acquisition device being integrated with a cellphone, a tablet computer, or a personal digital assistant (PDA), wherein the signal acquisition device comprises a button configured to be pressed against one side only of a body part or to have one side only of the body part pressed against it such that pressures are applied by the button to the body part or by the body part to the button,
a pressure sensor configured to measure the pressures that are applied by the button to the body part or by the body part to the button,
an optical sensor configured to detect flow of blood through the body part, wherein the processor is configured to determine a measurement of blood pressure from the applied pressures and the detected flow of blood when the applied pressures are applied in an order that does not generally increase or generally decrease or generally increase then generally decrease.

* * * * *